United States Patent
Kerwood et al.

(10) Patent No.: US 10,342,249 B2
(45) Date of Patent: Jul. 9, 2019

(54) STARCH COMPOSITIONS USEFUL FOR THICKENING AQUEOUS LIQUIDS

(71) Applicant: Tate & Lyle Ingredients Americas LLC, Hoffman Estates, IL (US)

(72) Inventors: Christopher C. Kerwood, Lafayette, IN (US); Marshall Hull, Lafayette, IN (US); William Skelding, Sycamore, IL (US); Marvin V. Wiederhold, West Lafayette, IN (US)

(73) Assignee: Tate & Lyle Ingredients Americas LLC, Hoffman Estates, IL (US)

( * ) Notice: Subject to any disclaimer, the term of this patent is extended or adjusted under 35 U.S.C. 154(b) by 0 days.

(21) Appl. No.: 15/313,629

(22) PCT Filed: May 27, 2015

(86) PCT No.: PCT/US2015/032654
§ 371 (c)(1),
(2) Date: Nov. 23, 2016

(87) PCT Pub. No.: WO2015/183939
PCT Pub. Date: Dec. 3, 2015

(65) Prior Publication Data
US 2017/0208851 A1    Jul. 27, 2017

Related U.S. Application Data

(60) Provisional application No. 62/003,467, filed on May 27, 2014.

(30) Foreign Application Priority Data

Aug. 5, 2014  (GB) .................................. 1413832.5

(51) Int. Cl.
| | |
|---|---|
| A23L 29/219 | (2016.01) |
| A23L 33/00 | (2016.01) |
| A23C 9/137 | (2006.01) |
| A23L 2/52 | (2006.01) |
| A61K 9/00 | (2006.01) |
| C08B 31/12 | (2006.01) |
| C08B 31/00 | (2006.01) |
| C08L 3/04 | (2006.01) |
| C08L 3/08 | (2006.01) |
| A23L 29/30 | (2016.01) |
| A61K 9/20 | (2006.01) |
| C08B 30/12 | (2006.01) |
| C08L 3/00 | (2006.01) |
| A23L 33/125 | (2016.01) |
| A61K 47/36 | (2006.01) |

(52) U.S. Cl.
CPC .............. *A23L 33/40* (2016.08); *A23C 9/137* (2013.01); *A23L 2/52* (2013.01); *A23L 29/219* (2016.08); *A23L 29/35* (2016.08); *A23L 33/00* (2016.08); *A23L 33/125* (2016.08); *A61K 9/00* (2013.01); *A61K 9/0095* (2013.01); *A61K 9/2059* (2013.01); *A61K 47/36* (2013.01); *C08B 30/12* (2013.01); *C08B 31/003* (2013.01); *C08B 31/006* (2013.01); *C08B 31/12* (2013.01); *C08L 3/00* (2013.01); *C08L 3/04* (2013.01); *C08L 3/08* (2013.01); *C12Y 302/00* (2013.01); *C12Y 304/00* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 3,505,110 A | 4/1970 | Kesler | |
| 3,951,947 A * | 4/1976 | Schanefelt | C08B 31/006 536/106 |
| 3,969,340 A * | 7/1976 | Tessler | C08B 31/006 536/106 |
| 4,120,983 A * | 10/1978 | Del Valle | A23L 3/00 127/70 |
| 4,303,451 A * | 12/1981 | Seidel | A23L 29/212 127/32 |
| 5,855,946 A * | 1/1999 | Seib | A21D 2/186 127/67 |

(Continued)

FOREIGN PATENT DOCUMENTS

WO    92/03936    3/1992

OTHER PUBLICATIONS

International Preliminary Report on Patentability in PCT/US2015/032654, dated Nov. 29, 2016.

*Primary Examiner* — Peter A Salamon
(74) *Attorney, Agent, or Firm* — McDonnell Boehnen Hulbert & Berghoff LLP

(57) ABSTRACT

The present invention relates specifically to starch products and starch compositions useful for thickening aqueous liquids, for example, for use by people suffering from dysphagia. In one aspect, the invention provides a pregelatinized, hydroxypropylated starch, having a level of hydroxypropylation in the range of about 1% to about 10%; an RVA viscosity in the range of about 400 cP to about 3500 cP; wherein the pregelatinized, hydroxypropylated starch is readily dispersible in milk. Another aspect provides a provides a pregelatinized, hydroxypropylated starch, having a level of hydroxypropylation in the range of about 1% to about 10%; and an RVA viscosity in the range of about 400 cP to about 3500 cP; and less than about 80%> of the surface protein of the corresponding native starch.

26 Claims, No Drawings

(56) References Cited

U.S. PATENT DOCUMENTS

| | | | |
|---|---|---|---|
| 6,221,420 B1* | 4/2001 | Thomas | A21D 2/186 426/578 |
| 6,299,907 B1* | 10/2001 | Seib | A21D 2/186 424/401 |
| 6,607,748 B1* | 8/2003 | Lenaerts | C08B 33/00 424/464 |
| 6,899,913 B1* | 5/2005 | Buwalda | A23C 9/1544 426/578 |
| 2002/0090446 A1* | 7/2002 | Jeffcoat | A23C 9/137 426/661 |
| 2006/0025381 A1* | 2/2006 | Brown | A21D 2/186 514/60 |
| 2006/0025382 A1* | 2/2006 | Brown | A21D 2/186 514/60 |
| 2006/0254737 A1* | 11/2006 | Anderson | C08B 31/003 162/175 |
| 2007/0039612 A1* | 2/2007 | Veelaert | C08B 30/12 127/65 |
| 2007/0102129 A1* | 5/2007 | Hwang | C08K 5/521 162/175 |
| 2007/0102130 A1* | 5/2007 | Satyavolu | C08L 3/00 162/179 |
| 2009/0107360 A1* | 4/2009 | Anderson | C08B 31/003 106/162.9 |
| 2011/0100256 A1* | 5/2011 | Anderson | C09D 103/02 106/126.1 |
| 2012/0231150 A1 | 9/2012 | Han | |
| 2017/0208851 A1* | 7/2017 | Kerwood | A23C 9/137 |

* cited by examiner

STARCH COMPOSITIONS USEFUL FOR THICKENING AQUEOUS LIQUIDS

CROSS-REFERENCE TO RELATED APPLICATIONS

This application is U.S. national phase application of International Patent Application no. PCT/US2015/032654 filed on May 27, 2015, which claims the benefit of priority of U.S. Provisional Patent Application No. 62/003,467, filed May 27, 2014, and UK Patent Application no. 1413832.5, filed Aug. 5, 2014, each of which is hereby incorporated herein by reference in its entirety.

BACKGROUND OF THE INVENTION

Field of the Invention

In certain aspects, the present invention relates generally to starch products and starch compositions. In more particular aspects, the present invention relates more specifically to starch products and starch compositions useful for thickening aqueous liquids, for example, for use by people suffering from dysphagia.

Technical Background

Difficulty or discomfort in swallowing is known as dysphagia. Dysphagia can accompany a wide variety of conditions, such as blunt throat injury, surgery caused impairment, stroke, multiple sclerosis, Asperger's syndrome, esophageal cancer, laryngeal cancer, Chagus disease, celiac, cystic fibrosis, Huntington's disease, Niemann-Pick disease, neurological conditions such as amyotrophic lateral sclerosis, Alzheimer's disease, Parkinson's disease, obesity, Riley-Day syndrome, high cholesterol, scleroderma, and diabetes. People with dysphagia generally lack the ability to properly seal the windpipe or to propel an entire bolus of food and/or beverage to the stomach. Accordingly, dysphagic people are at risk of having food or beverages being misrouted into their lungs, which presents the risk of bacterial infection, pneumonia, and even asphyxiation.

Dysphagia can be especially problematic with respect to the swallowing of liquids. Due to their low viscosity, they are especially susceptible to dripping into the lungs. Thickening such liquids for consumption is a common method of addressing this problem. Thickening also helps provide better bolus control and provides greater oral stimulation, which can also help manage the symptoms of dysphagia.

Modified food starches are often used to thicken liquids for dysphagia patients. Most conveniently, thickening can be performed at the time of service, for example by the addition of a dry powder to a desired liquid followed by agitation. Starches, however, can be difficult to homogeneously mix into a liquid. For example, in many cases the starch wets quickly, forming stringy, glue-like masses, potentially trapping some of the dry material in pockets to form "fish eyes" or powder clumps These attributes can be highly displeasing to the consumer. Accordingly, it is desirable to have a starch thickening agent that combines homogeneously with a liquid quickly with minimal stirring. This can be especially difficult when the liquid is milk; the complex nature of the fat and protein suspension present in milk makes the dispersion properties of the starch difficult to predict, especially with respect to process variability in large-scale manufacture. These issues have ultimately made the provision of a reliably milk-dispersible starch thickener difficult.

Thus, there remains a need for an improved starch thickener that is reliably and readily milk-dispersible.

SUMMARY OF THE INVENTION

One aspect of the invention is a pregelatinized, hydroxypropylated starch, having
a level of hydroxypropylation in the range of about 1% to about 10%; and
an RVA viscosity in the range of about 400 cP to about 3500 cP;
wherein the pregelatinized, hydroxypropylated starch is readily dispersible in milk.

Another aspect of the invention is a pregelatinized, hydroxypropylated starch, having
a level of hydroxypropylation in the range of about 1% to about 10%;
an RVA viscosity in the range of about 400 cP to about 3500 cP; and
less than about 80% of the surface protein of the corresponding native starch.

Another aspect of the invention is a method for making a pregelatinized, hydroxypropylated starch including
hydroxypropylating a starch and surface treating the starch to provide a hydroxypropylated starch, and
gelatinizing the hydroxypropylated starch.
The method can further include cross-linking the starch before the gelatinizing, and/or agglomerating the gelatinized material.

Another aspect of the invention is a pregelatinized, hydroxypropylated starch prepared by a process including
hydroxypropylating a starch and surface treating the starch to provide a hydroxypropylated starch, and
gelatinizing the hydroxypropylated starch.
The method can further include cross-linking the starch before the gelatinizing, and/or agglomerating the gelatinized material.

Another aspect of the invention is a starch composition including a pregelatinized, hydroxypropylated starch as described herein.

Another aspect of the invention is a method for thickening an aqueous liquid, the method comprising dispersing the starch composition as described herein in the liquid to provide a substantially homogeneous thickened liquid.

DETAILED DESCRIPTION OF THE INVENTION

In one aspect, the invention provides a pregelatinized hydroxypropylated starch useful, for example, in thickening liquids, for example, potable liquids such as beverages and broths. The pregelatinized hydroxypropylated starch can have, for example, a level of hydroxypropylation in the range of about 1% to about 10%; and an RVA viscosity in the range of about 400 cP to about 3500 cP. Notably, in certain embodiments, the starch composition is readily dispersible in milk.

As the person of ordinary skill in the art will appreciate, the level of hydroxypropylation is calculated as a weight percent based on the weight of the dry starch. The level of hydroxypropylation can be varied by the person of ordinary skill in the art based on the description herein, depending on the desired properties of the ultimate hydroxypropylated, pregelatinized starch. For example, in certain embodiments of the hydroxypropylated, pregelatinized starches as described herein, the level of hydroxypropylation is in the range of about 1% to about 10%. In certain particular embodiments of the hydroxypropylated, pregelatinized starches as described herein, the level of hydroxypropylation is in the range of about 1% to about 8%, or in the range of about 1.5% to about 6%, or in the range of about 2% to about 5%. In other embodiments of the compositions as described herein the level of hydroxypropylation is in the range of about 1% to about 5%, or in the range of about 1% to about 6%, or in the range of about 1.5% to about 5%, or in the range of about 1.5% to about 8%, or in the range of about 1.5% to about 10%, or in the range of about 2% to about 6%, or in the range of about 2% to about 8%, or in the range of about 2% to about 10%.

As the person of ordinary skill in the art will appreciate, the viscosity of the pregelatinized hydroxypropylated starch can be determined as its RVA viscosity. The RVA viscosity is defined as the viscosity measured by the following procedure, using a Rapid Visco Analyzer Model RVA-4. 1.85 g material to be measured, 4.5 g of propylene glycol and 25.65 g of a pH 6.5 buffer are added to the instrument cup to make a 5.5% dry solids basis aqueous mixture. The instrument mixing parameters are as follows: mix at 700 rpm for 1 minute and 160 rpm for 47 minutes. The instrument temperature parameters are as follows: 15 minutes at 35° C., heating from 35° C. to 95° C. for 7 minutes, 10 minutes hold at 95° C., cooling from 95° C. to 35° C. for 6 minutes, 10 minutes hold at 35° C., for a total of 48 minutes. The Initial viscosity is the measurement at time=14.7 minutes. The final viscosity, used herein as the RVA viscosity, is the measurement at time=47.4 minutes.

The RVA viscosity can be varied by the person of ordinary skill in the art based on the description herein, depending on the desired properties of the ultimate hydroxypropylated, pregelatinized starch. For example, in certain embodiments of the compositions as described herein, the RVA viscosity of the pregelatinized, hydroxypropylated starch is in the range of about 400 cP to about 3500 cP. For example, in certain particular embodiments of the hydroxypropylated, pregelatinized starches as described herein, the RVA viscosity is in the range of about 700 cP to about 2500 cP, or in the range of about 400 cP to about 3000 cP, or in the range of about 400 cP to about 2500 cP, or in the range of about 400 cP to about 2000 cP, or in the range of about 700 cP to about 3500 cP, or in the range of about 700 cP to about 3000 cP, or in the range of about 700 cP to about 2000 cP.

For example, in certain embodiments, the hydroxypropylated, pregelatinized starch is cross-linked. The amount and type of cross-linking can be selected by the person of ordinary skill in the art to provide the desired viscosity to the hydroxypropylated, pregelatinized starch. The starch can be cross-linked in a variety of fashions. For example, in certain embodiments, the starch is cross-linked by phosphate (e.g., by a mono- or polyphosphate bridge, formed, for example, by treating the starch with $POCl_3$, or in other embodiments with alkali trimetaphosphate or tripolyphosphate). In other embodiments, the starch is crosslinked by an alkylene cross-linker (e.g., as formed by reaction with epichlorohydrin), or a dicarboxylate cross-linker. The person of ordinary skill in the art will select the appropriate crosslinker(s) based on the description herein to provide the desired properties to the pregelatinized hydroxypropylated starch.

In certain embodiments, the hydroxypropylated, pregelatinized starches described herein are readily dispersible in milk. As used herein, "readily dispersible in milk" means that a material passes the following described test: 6.5 g of the material is added to 118 g of 2% milk, then allowed to sit for 10 seconds, then stirred by hand for 10 seconds with a long-handled spoon. The stirred sample is allowed to sit for 40 seconds, and then is poured through a 10 Mesh sieve. To pass the test, the entire mixture will pour through the sieve without lumps being retained on the sieve.

The present inventors have determined that, in certain embodiments, reduction of the amount of protein at the surface of the starch granules can greatly improve the dispersibility of the hydroxypropylated, pregelatinized starch. Accordingly, in certain embodiments of the pregelatinized hydroxypropylated starches as described herein, the pregelatinized, hydroxypropylated starch has less than about 80%, less than about 50%, or even less than about 20% of the surface protein of the corresponding native starch. As the person of ordinary skill will appreciate, the pregelatinized, hydroxypropylated starch will have a corresponding native starch from which it is derived. Examples of native starches are described in more detail below. The surface protein of a starch can be measured As described in more detail below, the amount of protein can be reduced in a number of fashions, for example, by treatment with enzymes such as proteases and amylases treatment with acid, treatment with base or mechanical abrasion.

The hydroxypropylated, pregelatinized starch can be provided, for example, in a granular or powder solid form. In certain embodiments, the hydroxypropylated, pregelatinized starch has a moisture level in the range of about 2% to about 15% (i.e., by weight). For example, in certain embodiments, the hydroxypropylated, pregelatinized starch has a moisture level in the range of about 4% to about 7%. In other embodiments, the starch composition has a moisture level in the range of about 6% to about 10%, or in the range of about 7.5% to about 10%, or in the range of about 6% to about 15%, or in the range of about 7.5% to about 15%, or in the range of about 6% to about 8.5%, or in the range of about 7.5% to about 8.5%. The inventors have determined that dispersibility, especially in milk, can be improved when the moisture content is greater than about 7.5%.

In certain embodiments of the starch compositions described herein, the hydroxypropylated, pregelatinized starch has a bulk density in the range of about 13 $lb/ft^3$ to about 20 $lb/ft^3$, for example, in the range of about 14 $lb/ft^3$ to about 16 $lb/ft^3$. In certain embodiments of the hydroxypropylated, pregelatinized starches described herein, the hydroxypropylated, pregelatinized starch has a particle size distribution such that 70% of the composition is retained between a U.S. #30 screen and a U.S. #120 screen. Moreover, certain desirable embodiments of the hydroxypropylated, pregelatinized starch materials as described herein are substantially free of fines. As used herein, "fines" are particles having a maximum diameter less than 125 μm. In one embodiment, the hydroxypropylated, pregelatinized starch has less than about 15%, less than about 10%, less than 8% or even less than about 5% fines. Of course, as the person of ordinary skill will appreciate, it may not be necessary to remove all fines from the product. For example, in certain embodiments, the hydroxypropylated, pregelatinized starch includes greater than about 0.1%, greater than about 0.5%, greater than 1% or even greater than about 3% fines.

In certain embodiments, to provide desirable moisture levels, densities and particle sizes, the pregelatinized, hydroxypropylated starch can be provided in agglomerated form. The person of ordinary skill in the art will adjust conventional agglomeration techniques to provide the desired properties (e.g., particle sizes, densities, moisture levels and amounts of fines) to the hydroxypropylated, pregelatinized starch.

As described throughout this disclosure, and in more detail below, the starch product is pregelatinized, that is, it is gelatinized and dried by the manufacturer in the formulation process. Pregelatinized starches develop viscosity when dispersed in cold or warm water, without the need for further intense heating. Pregelatinized starch is also known in the art as precooked starch, pregelled starch, instant starch, cold water soluble starch, and cold water swelling starch.

As described above, in certain embodiments, the pregelatinized, hydroxypropylated starch is substantially gelatinized (e.g., at least about 75%, at least about 80%, or even at least about 85% gelatinized). In certain embodiments, the degree of gelatinization of the starch is in the range of about 75% to about 99%, about 80% to about 99%, or about 85% to about 99%). The person of ordinary skill in the art will determine the degree of gelatinization using differential scanning calorimetry ("DSC"). To perform the measurement, the pregelatinized hydroxypropylated starch is milled to a particle size smaller than 200 µm and mixed with water to a moisture content of 65%. Next, the product is heated in the DSC device from 10° C. to 100° C. at a rate of 10° C. per minute and the enthalpy of fusion in the range between 55° C. and 85° C. is evaluated and compared with the enthalpy of fusion of the raw, i.e. non-gelatinized, hydroxypropylated starch. As described in more detail below, the starch can be gelatinized by cooking the starch, e.g., via steam-injected spray cooking.

The person of ordinary skill in the art will appreciate that the pregelatinized, hydroxypropylated starches described herein can be based upon a variety of types of starches. The person of ordinary skill in the art can select the particular starch based on the description herein, based on its performance, availability and cost, and the desired properties of the pregelatinized, hydroxypropylated starch.

For example, the pregelatinized, hydroxypropylated starches described herein can be based starches derived from any native source. A native starch as used herein, is one as it is found in a plant, including starches derived from a plant obtained by standard breeding techniques including cross-breeding, translocation, inversion, transformation, insertion, irradiation, chemical or other induced mutation, or any other method of gene or chromosome engineering to include variations thereof. In addition, starch derived from a plant grown from induced mutations and variations of the above generic composition which may be produced by known standard methods of mutation breeding are also suitable for use as native starches. Starches can be derived from a variety of sources, such as from cereals, tubers and roots, legumes and fruits. Typical sources or starch include, but are not limited to, corn, potato, sweet potato, wheat, tapioca, pea, banana, plantain, barley, oat, rye, triticale, sago, amaranth, arrowroot, canna, sorghum, and rice, and can include low amylose (waxy) and high amylose varieties thereof. In one embodiment, the pregelatinized, hydroxypropylated starch is based on corn starch, for example, waxy corn starch.

In certain embodiments of the pregelatinized, hydroxypropylated starches as described herein, the starch has a high level of amylopectin as compared to amylose. For example, in certain embodiments, the polysaccharide component of the starch is at least about 80% amylopectin, at least about 90% amylopectin, at least about 95% amylopectin, at least about 98% amylopectin, or even at least about 99% amylopectin. For example, the starch may be a waxy starch, such as waxy corn starch or waxy potato starch. One of skill in the art will also recognize that commercial starches often comprise some level of contamination with other starches. For example, commercial waxy corn starch can contain several percent dent corn starch contamination. For example, a commercial waxy corn starch may comprise less than about 10% or less than about 7% dent starch due to contamination. Of course, the person of ordinary skill in the art can select other varieties of starch, or mixtures of varieties of starch, to provide the desired properties to the pregelatinized, hydroxypropylated starches described herein.

The pregelatinized, hydroxypropylated starches described herein can be prepared using a number of techniques. For example, in certain embodiments, the pregelatinized, hydroxypropylated starch is prepared by a process comprising hydroxypropylating a starch and surface treating the starch to provide a hydroxypropylated starch. The surface treatment and the hydroxypropylation can be performed in any order, with other steps optionally intervening. For example, in one embodiment, the hydroxypropylation is performed before the surface treatment. In certain embodiments, for example, in order to provide the desired viscosity characteristics to the pregelatinized, hydroxypropylated starch, the starch is cross-linked, for example, before the surface treatment. In one such embodiment, the hydroxypropylated starch is cross-linked before the surface treatment.

The hydroxypropylation of the starch can be performed using conventional hydroxypropylation techniques, for example, by treatment with propylene oxide under basic conditions. The starch can be brought to a highly basic pH (for example, in the range of about 8.5 to about 12.5, for example, from about 10 to about 12.5), and treated with propylene oxide under time and temperature conditions suitable to provide the desired level of hydroxypropylation. The pH can be adjusted with any of a variety of, for example, alkali or alkaline earth metal salts, such as disodium phosphate, trisodium phosphate, sodium hydroxide, potassium hydroxide and calcium hydroxide, for example, at a level in the range of about 0.002 to about 0.030 parts by weight of sodium hydroxide or the equivalent of another alkali for every part of starch used. Moreover, a processing aid such as sodium sulfate, magnesium sulfate, disodium orthophosphate, and trisodium orthophosphate, can be added, for example, at a level in the range of about 0.001 to about 0.150 parts by weight of the aid are used per part of starch. The hydroxypropylation reaction can be conducted at a variety of temperatures (e.g., 20-100° C.) for a variety of times (e.g., 3-36 hours) at a variety of pressures (e.g., 0.5-5 atmospheres, or about ambient atmosphere), depending on the starch and the desired level of hydroxypropylation. In one example of a process for hydroxypropylating starch, waxy corn starch, water, sodium sulfate and sodium hydroxide are combined at 43.3° C. (110° F.) to provide a pH of 11.6, and reacted with propylene oxide at 43.3° C. (110° F.) for 20-24 hours. Excess propylene oxide can be removed using conventional techniques.

The cross-linking of the starch can also be performed, for example, using any conventional method. Cross-linking agents bind neighboring anhydroglucose units in the amorphous regions of the starch (e.g., of the amylopectin). Cross-links prevent the granules from fully swelling and ultimately disintegrating. The covalent cross-link network also makes the granules tolerant to pH extremes and high shear processes common to food manufacturing. A variety of cross-linking agents can be used, for example, bifunctional etherifying and/or esterifying agents such as epichlorohydrin, bis-β-chloroethyl ether, dibasic organic acid equivalents like adipic anhydride, phosphorus oxychloride ($POCl_3$), trimetaphosphate and polyphosphate (e.g., the alkali and alkaline earth metal salts thereof), linear mixed anhydrides of acetic and di- or tribasic carboxylic acids. Another useful crosslinking agent is sodium hypochlorite, which when used in the proper amount and under proper pH conditions (e.g., 11 or more) provides crosslinked starch. In certain embodiments of the starch compositions as described herein. The cross-linking reaction can be performed under a variety of conditions. For example, cross-linking with POCl$_3$ can be performed at highly basic pH (for example, in the range of about 8.5 to about 12.5, for example, from about 10 to about 12.5, e.g., at pH 11.6) at a variety of temperatures (for example, 10-100° C., 20-65° C., e.g., 43.3° C. (110° F.)) for sufficient time to provide the desired level of cross-linking, after which time the reaction can be quenched by reducing the pH (e.g., to about 6.5) with acid (e.g., hydrochloric acid, phosphoric acid, sulfuric acid). Cross-linking of starch is described further in "Starch Derivatives: Production and Uses" by M. Rutenberg and D. Solarek, Starch: Chemistry and Technology, Chapter X, pp. 324-332, 1984, as well as in U.S. Pat. Nos. 2,328,537 and 2,801,242. As the person of ordinary skill in the art will appreciate, the cross-linking of the starch can be performed before or after the hydroxypropylation.

In certain embodiments, other modifications may be present in the pregelatinized, hydroxypropylated starch. Examples of such modifications will be familiar to the person of ordinary skill in the art. Certain such modifications are described, for example, in 21 C.F.R. 172.892, which is hereby incorporated herein by reference in its entirety. Examples include modification by 1-octenyl succinic anhydride, acetic anhydride, vinyl acetate, acrolein, succinic anhydride, and bleaching by various oxidizing agents. Such modifications are well-known to the person of ordinary skill in the art, and are described, for example, in MODIFIED STARCHES: PROPERTIES AND USES, Ed. Wurzburg, CRC Press, Inc., Florida (1986). Any additional modifications are, in certain embodiments, provided at levels less than about 10 wt %, less than about 5 wt %, less than about 2 wt %, less than about 1 wt %, or even less than 0.5 wt % in the pregelatinized, hydroxypropylated starch. In certain alternative embodiments, however, substantially no additional modifications are present.

As noted above, the starch is also surface treated, for example, to help to provide the product pregelatinized, hydroxypropylated starch with dispersible character. The surface treatment may be performed in a variety of fashions, as described in more detail below. The surface treatment can be performed, for example, before gelatinization. And as noted above, in certain embodiments of the pregelatinized, hydroxypropylated starch described herein, the starch granules have substantially reduced protein at their surfaces (e.g., less than about 80%, less than about 50%, or less than about 20% of the surface protein of the corresponding native starch). The person of ordinary skill in the art can perform the surface treatments described herein to provide the desired level of surface protein to the pregelatinized, hydroxypropylated starch. For example, a surface treatment can be performed under conditions and for a time sufficient to remove at least about 20%, at least about 50%, or even at least about 80% of the starch from the surface of the starch (i.e., as compared to the material on which the surface treatment is performed).

For example, in certain embodiments of the pregelatinized, hydroxypropylated starches as described herein, the starch is treated (e.g., either before or after hydroxypropylation, and either before or after cross-linking), with a protease. The protease treatment can be performed under conditions sufficient to substantially reduce the amount of protein as described above, or to otherwise improve the dispersibility of the product pregelatinized, hydroxypropylated starch (e.g., to provide a milk-dispersible starch). Examples of suitable proteases include, for example, thermolysin, pepsin, Arg-C, elastase and trypsin. For example, starch can be subjected to treatment with thermolysin at elevated temperature (e.g., 35-75° C., 50-70° C., or about 64° C.) for several hours (e.g., 1-10, 2-8, or about 4) to remove an amount of protein from the surface of the starch granule, or to otherwise improve the dispersibility of the product pregelatinized, hydroxypropylated starch (e.g., to provide a milk-dispersible starch). The person of ordinary skill in the art will develop procedures for protease treatment based on enzymatic digestion procedures known in the art.

In other embodiments of the pregelatinized, hydroxypropylated starches as described herein, the starch is treated (e.g., either before or after hydroxypropylation, and either before or after cross-linking) with a carbohydrase such as an amylase. The carbohydrase or amylase treatment can be performed under conditions sufficient to substantially reduce the amount of protein as described above, or to otherwise improve the dispersibility of the product pregelatinized, hydroxypropylated starch (e.g., to provide a milk-dispersible starch). The carbohydrase treatment can be performed, for example, under conditions to remove a surface layer of the starch granules, thereby removing the surface protein along with the surface layer. Examples of suitable carbohydrases include, for example, batalase, α-amylase, β-amylase and γ-amylase; as the person of ordinary skill in the art, carbohydrases can be used in combination, sequentially or concomitantly. The person of ordinary skill in the art will develop procedures for carbohydrase treatment based on enzymatic digestion procedures known in the art.

In other embodiments, the surface treatment is a treatment with acid (e.g., either before or after hydroxypropylation, and either before or after cross-linking) under conditions sufficient to substantially reduce the amount of protein as described above, or to otherwise improve the dispersibility of the product pregelatinized, hydroxypropylated starch (e.g., to provide a milk-dispersible starch). Acid treatment can be performed such that it does not reduce the viscosity of the pregelatinized, hydroxypropylated starch to unsuitable levels, especially when the starch is cross-linked before acid treatment. For example, the starch can be treated in an aqueous medium at a pH no greater than about 3, or even no greater than about 2 (e.g., about 1 to about 2.5, about 1.3 to about 2, about 2, about 1.5, or about 1) with a strong acid (e.g., hydrochloric acid, sulfuric acid) at a temperature and for a time sufficient to reduce the amount of protein as described above, or to otherwise improve the dispersibility of the product pregelatinized, hydroxypropylated starch (e.g., to provide a milk-dispersible starch). For example, the treatment can be performed at a variety of temperatures (e.g., 20-100° C., or 30-80° C., or 35-55° C.) for a variety of times (e.g., 3-36 hours, or 4-20 hours, or 6-10 hours) at a variety of pressures (e.g., 0.5-5 atmospheres, or about ambient atmosphere). The acid treatment can be performed, for example, under conditions to remove a surface layer of the starch granules, thereby removing the surface protein along with the surface layer. A variety of strong acids can be used to adjust the pH, for example, hydrochloric, sulfuric, or phosphoric acids. When the desired level of reaction is attained, the reaction mixture can be substantially neutralized (e.g., to a pH in the range of about 5.5 to about 8.5, e.g., about 6.5, about 7, or about 7.5) with a suitable base (e.g., alkali or alkaline earth metal hydroxide, carbonate, bicarbonate, such as sodium carbonate, sodium hydroxide or sodium bicarbonate).

Of course, other surface treatment techniques can be used to reduce the amount of protein at the surface of the starch, or to otherwise improve the dispersibility of the product pregelatinized, hydroxypropylated starch (e.g., to provide a milk-dispersible starch). For example, in one embodiment, the surface treatment is a mechanical polishing, performed under conditions sufficient to reduce the amount of protein at the surface of the starch, or to otherwise improve the dispersibility of the product pregelatinized, hydroxypropylated starch (e.g., to provide a milk-dispersible starch).

After any of the reactions described herein, the starch product or intermediate can be washed to substantially remove impurities, for example, those introduced in the modification, cross-linking and/or surface treatment operations described herein. As the person of ordinary skill in the art will appreciate, a variety of methods and apparatuses can be used to wash the starch product or intermediate. For example, the starch product or intermediate can be washed one or more times using water, dilute acid, dilute base or buffer, optionally with a surfactant added, and separated from the washing liquid using centrifugation, filtration or settling. An example of a centrifuge device useful in washing the starch product or intermediate is the Merco nozzle centrifuge.

Similarly, the starch products described herein may be purified, at any intermediate or final product stage, by any method known in the art to remove starch off flavors, odors, or colors that are native to the starch or created during processing. Suitable purification processes for treating starches are disclosed in European Patent Application Publication no. 554 818. Alkali washing techniques are also useful. Examples of such washing techniques are described in U.S. Pat. Nos. 4,477,480 and 5,187,272.

The desired degree of gelatinization can be achieved by cooking the starch. For example, in certain embodiments, the hydroxypropylated, surface-treated starch is substantially gelatinized (e.g., to a degree as described above) by spray cooking. The person of ordinary skill in the art will appreciate that the spray cooking can be performed in a variety of ways using a variety of devices. For example, in certain embodiments, the spray cooking is performed using a two-phase, steam-injected spray cooking nozzle, such as those available from Spraying Systems Co. and Delevan Spray Technologies. The person of ordinary skill in the art will adapt conventional spray drying processes to provide the desired spray-cooked product. The process can be performed, for example, with a starch slurry at a pH in the range of about 4.5 to about 6. The process can be performed, for example, at a nozzle inlet temperature in the range of about 204.4° C. (400° F.) to about 273.9° C. (525° F.) (e.g., about 425° F., about 450° F., about 475° F. or about 500° F.); and a nozzle outlet temperature in the range of about 79.4° C. (175° F.) to about 126.7° C. (260° F.) (for example, about 195° F., about 210° F., about 230° F. or about 250° F.). The process can be performed, for example, at a pressure in the range of about 3500 psig to about 5500 psig, e.g., about 4000 psig to about 5000 psig. The steam pressure can be, for example, in the range of about 130 psig to about 165 psig, e.g., about 140 to about 155 psig. An embodiment of a spray cooking process is described in U.S. Pat. No. 4,280,851, which is hereby incorporated herein by reference in its entirety; the person of ordinary skill in the art will appreciate that other spray cooking processes can be adapted for use. Notably, in certain embodiments, the spray-cooked product is a substantially dry solid (e.g., in the form of a fine powder), having a moisture level in the range of about 4% to about 7%.

Of course, the person of ordinary skill in the art will appreciate that other methods can be used to cook and dry the starch. For example, the person of ordinary skill the art will appreciate that the hydroxypropylated, surface-treated starch may alternatively be cooked and dried in different operations. For example, in certain embodiments, the hydroxypropylated, surface-treated starch is first cooked to provide the desired degree of gelatinization, then dried to provide the desired moisture level. A variety of types of cooking processes can be used, for example, jet-cooking and spray cooking. Desirably, moisture (e.g., in the form of steam) is present in the cooking process to assist in gelatinization. A variety of drying techniques can be used to provide the dried product, for example, spray drying, flash drying, tray drying and drum drying. The dried product can be, for example, a substantially dry solid, having a moisture level in the range of about 4% to about 7%. The person of ordinary skill in the art can adapt conventional cooking and drying procedures to provide the desired degree of gelatinization and the desired moisture content.

In certain embodiments of the starch compositions as described herein, the pregelatinized, hydroxypropylated starch (e.g., the dry product as described above) is agglomerated to provide an agglomerated, hydroxypropylated, pregelatinized starch. Agglomeration can be performed using any of a variety of methods familiar to the person of ordinary skill in the art, for example, rewet agglomeration using, e.g., a Glatt fluid bed agglomerator. The person of ordinary skill in the art can adjust agglomeration conditions in order to provide the desired moisture, particle size and bulk density properties to the material, as described above. The agglomeration can be performed, for example, to provide materials having a moisture content in the range of 6% to about 10%, or in the range of about 7.5% to about 10%, or in the range of about 6% to about 15%, or in the range of about 7.5% to about 15%, or in the range of about 6% to about 8.5%, or in the range of about 7.5% to about 8.5%. Similarly, the agglomeration can be performed such that the agglomerated material has a bulk density in the range of about 13 lb/ft$^3$ to about 20 lb/ft$^3$, for example, in the range of about 14 lb/ft$^3$ to about 16 lb/ft$^3$. Similarly, the agglomeration can be performed such that 70% of the agglomerated material is retained between a U.S. #30 screen and a U.S. #120 screen. The agglomeration can also be performed to provide a material that is substantially free of fines. In one embodiment, the agglomerated, hydroxypropylated, pregelatinized starch has less than about 15%, less than about 10%, less than 8% or even less than about 5% fines. Of course, as the person of ordinary skill will appreciate, it may not be necessary to remove all fines from the product. For example, in certain embodiments, the agglomerated, hydroxypropylated, pregelatinized starch includes greater than about 0.1%, greater than about 0.5%, greater than 1% or even greater than about 3% fines.

In certain embodiments, the pregelatinized, hydroxypropylated starch (e.g., the dry product as described above) is milled before agglomeration, for example, to provide a relatively uniform sized particulate for agglomeration. The type and degree milling can be selected by the person of ordinary skill in the art based on routine experimentation.

Of course, the person of ordinary skill in the art will appreciate that other methods and apparatuses can be used to provide agglomerates. For example, U.S. Pat. No. 4,871,398, which is hereby incorporated herein by reference in its entirety, describes a continuous method for preparing gelatinized spray-dried starch agglomerates. This method uses two or more capped, two-fluid nozzles of the type described in U.S. Pat. No. 4,280,851. Two or more nozzles are aligned in a drying tower such that their spray patterns intersect. The point of intersection is distant enough from the nozzles to avoid clumping, but close enough to the nozzles so that the particle surfaces are sufficiently tacky to effect adhesion of particles into agglomerates.

The methods described herein can be adapted by the person of ordinary skill in the art to provide pregelatinized, hydroxypropylated starches having the properties as described herein.

The pregelatinized, hydroxypropylated starches described herein can be formulated into a variety of starch compositions. Accordingly, one embodiment of the invention is a starch composition including a pregelatinized, hydroxypropylated starch as described herein. For example, in certain embodiments, the starch composition consists of, or consists essentially of the pregelatinized, hydroxypropylated starch. Of course, the person of ordinary skill in the art will appreciate that other components may be included in the starch composition, such as nutrients and flavorings. In certain embodiments, the starch composition includes at least about 80%, at least about 85%, at least about 90%, at least about 95%, at least about 98% or even at least about 99% of the pregelatinized, hydroxypropylated starch as described herein.

In certain embodiments of the starch compositions as described herein, the starch composition is substantially free of maltodextrin. The inventors have determined that addition of maltodextrin, while theoretically helpful in improving milk dispersibility, can introduce severe process and product inconsistencies (e.g., with respect to pH stability, flowability, loose bulk density, viscosity, consistency), providing products that have unreliable dispersibility. In certain embodiments of the starch compositions as described herein, the starch composition has less than about 5%, less than about 3%, less than about 2%, less than about 1%, less than about 0.1%, or even less than about 0.05% maltodextrin.

Another aspect of the invention is a method for thickening an aqueous liquid. The method includes dispersing a starch composition as described herein in the liquid to provide a substantially homogenous thickened liquid. As used herein, the substantially homogeneous thickened liquid will pass through a 10 Mesh sieve without lumps due to the starch being retained on the sieve. Desirably, the starch composition is agitated in the liquid for no more than 5 minutes (e.g., no more than 4 minutes, no more than 3 minutes, no more than 2 minutes, no more than 90 seconds, or even no more than one minute) to provide the substantially homogenous thickened liquid. Desirably, the dispersing process takes less than about 6 minutes (e.g., no more than 5 minutes, no more than 4 minutes, no more than 3 minutes, no more than 2 minutes, or even no more than 90 seconds). In certain embodiments, the starch composition is added to the liquid at a rate in the range of about 15 mL to about 50 mL per 250 mL liquid. In certain desirable embodiments, the liquid is at a temperature in the range of about 5° C. to about 30° C. when the starch composition is dispersed therein.

As the person of ordinary skill in the art will appreciate, a variety of aqueous liquids can be thickened using the starch compositions described herein. For example, in one embodiment, the liquid is a potable liquid. Thickening of potable liquids can be especially useful for those suffering from dysphagia, as described above. Examples of liquids that can be thickened as described herein include, for example, water, beverages, soups, broths, sauces, gravies, syrups, dressings, medications and nutritional supplements. For example, in one embodiment, the liquid is milk. In another embodiment, the liquid is water.

It will be apparent to those skilled in the art that various modifications and variations can be made to the present invention without departing from the scope of the invention. Thus, it is intended that the present invention cover the modifications and variations of this invention provided they come within the scope of the appended claims and their equivalents.

What is claimed is:

1. A pregelatinized, hydroxypropylated starch, having
a level of hydroxypropylation in the range of about 1% to about 10%;
an RVA viscosity in the range of about 400 cP to about 3500 cP; and
an amount of surface protein that is less than about 80% of an amount of surface protein of the corresponding native starch,
the pregelatinized, hydroxypropylated starch being prepared by a process comprising
hydroxypropylating a starch and surface treating the starch to provide a hydroxypropylated starch, and
gelatinizing the hydroxypropylated starch.

2. The pregelatinized, hydroxypropylated starch according to claim 1, wherein the pregelatinized, hydroxypropylated starch is readily dispersible in milk.

3. The pregelatinized, hydroxypropylated starch according to claim 1, having an amount of surface protein that is less than about 50% of the amount of surface protein of the corresponding native starch.

4. The pregelatinized, hydroxypropylated starch according to claim 1, wherein the pregelatinized hydroxypropylated starch is in agglomerated form.

5. The pregelatinized, hydroxypropylated starch according to claim 1, having a moisture level in the range of about 2% to about 15%.

6. The pregelatinized, hydroxypropylated starch according to claim 1 having a bulk density in the range of about 16 lb/ft$^3$ to about 18 lb/ft$^3$, and wherein 70% of the composition is retained between a U.S. #30 screen and a U.S. #120 screen.

7. The pregelatinized, hydroxypropylated starch according to claim 1, wherein the pregelatinized hydroxypropylated starch has hydroxypropyl substitution in the range of about 1% to about 8%.

8. The pregelatinized, hydroxypropylated starch according to claim 1, wherein the pregelatinized, hydroxypropylated starch is cross-linked.

9. The pregelatinized, hydroxypropylated starch according to claim 1, wherein the pregelatinized hydroxypropylated starch has an RVA viscosity in the range of about 700 cP to about 2500 cP.

10. The pregelatinized, hydroxypropylated starch according to claim 1, wherein the pregelatinized hydroxypropylated starch is based on a corn starch.

11. The pregelatinized, hydroxypropylated starch according to claim 1, wherein the amount of any additional modifications to the starch other than hydroxypropylation and cross-linking are at a level of less than about 1 wt %.

12. The pregelatinized, hydroxypropylated starch according to claim 1, wherein the hydroxypropylation is performed before the surface treatment.

13. The pregelatinized, hydroxypropylated starch according to claim 1, wherein the method further comprises cross-linking the starch.

14. The pregelatinized, hydroxypropylated starch according to claim 1, wherein the surface treatment is a treatment with a protease.

15. The pregelatinized, hydroxypropylated starch according to claim 1, wherein the surface treatment is a treatment with acid at a pH less than 3 under conditions to remove a surface layer of the starch granules.

16. The pregelatinized, hydroxypropylated starch according to claim 1, wherein the surface treatment is a mechanical polishing.

17. The pregelatinized, hydroxypropylated starch according to claim 1, wherein the surface treatment is a treatment with a carbohydrase.

18. A starch composition comprising the pregelatinized, hydroxypropylated starch according to claim 1.

19. The starch composition according to claim 18, comprising at least about 90 wt % of the pregelatinized hydroxypropylated starch.

20. The starch composition according to claim 18, wherein the starch composition is substantially free of maltodextrin.

21. A method for making a pregelatinized, hydroxypropylated starch according to claim 1, the method comprising
hydroxypropylating a starch and surface treating the starch to remove at least 20% of surface protein of the starch to provide a hydroxypropylated starch, and
gelatinizing the hydroxypropylated starch to form the pregelatinized, hydroxypropylated starch.

22. A method for thickening an aqueous liquid, the method comprising dispersing the starch composition according to claim 18 in the liquid to provide a substantially homogeneous thickened liquid.

23. The method according to claim 22, wherein the liquid is selected from the group consisting of water, beverages, soups, broths, sauces, gravies, syrups, dressings, medications and nutritional supplements.

24. The method according to claim 22, wherein the liquid is at a temperature in the range of about 5° C. to about 30° C., and wherein the starch composition is agitated in the liquid for no more than 3 minutes to provide the substantially homogenous thickened liquid.

25. The pregelatinized, hydroxypropylated starch according to claim 1,
having an amount of surface protein that is less than about 50% of the amount of surface protein of the corresponding native starch;
in agglomerated form;
having a moisture level in the range of about 2% to about 15%;
has hydroxypropyl substitution in the range of about 1% to about 8%;
in cross-linked form; and
having an RVA viscosity in the range of about 700 cP to about 2500 cP.

26. The pregelatinized, hydroxypropylated starch according to claim 25, wherein the pregelatinized, hydroxypropylated starch is readily dispersible in milk.

* * * * *